United States Patent [19]

Nickl et al.

[11] Patent Number: 4,678,792

[45] Date of Patent: Jul. 7, 1987

[54] QUATERNARY 3,4-DIHYDRO-ISOQUINOLINIUM SALTS

[75] Inventors: Josef Nickl; Erich Muller; Benthold Narr; Helmut Ballhause; Walter Haarmann, all of Biberach, Fed. Rep. of Germany

[73] Assignee: Dr. Karl Thomae GmbH, Biberach an der Riss, Fed. Rep. of Germany

[21] Appl. No.: 706,579

[22] Filed: Feb. 28, 1985

[30] Foreign Application Priority Data

Mar. 3, 1984 [DE] Fed. Rep. of Germany ....... 3407955

[51] Int. Cl.$^4$ .................................. A61K 31/47
[52] U.S. Cl. .................................. 514/307; 514/824
[58] Field of Search .................................. 514/307

[56] References Cited

U.S. PATENT DOCUMENTS 4,042,697  8/1977  Garside et al. .................. 514/307

*Primary Examiner*—Frederick E. Waddell
*Attorney, Agent, or Firm*—David E. Frankhouser; Alan R. Stempel

[57] ABSTRACT

This invention relates to a compound of formula (I)

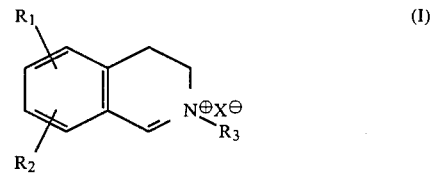

wherein $R_1$ and $R_2$ are each independently hydrogen, $C_1$-$C_3$ alkyl or $C_1$-$C_3$ alkoxy; and $R_3$ is a $C_7$-$C_9$ aralkyl, the phenyl nucleus of which can be mono-, di-, or tri-substituted by halogen, $C_1$-$C_3$ alkyl or $C_1$-$C_3$ alkoxy, and nontoxic, pharmaceutically acceptable salts thereof. The compounds have useful antithrombic properties.

15 Claims, No Drawings

QUATERNARY 3,4-DIHYDRO-ISOQUINOLINIUM SALTS

BACKGROUND OF THE INVENTION

Field of the Invention

The present invention relates to the field of 3,4-dihydroisoquinolinium compounds and their use as pharmaceutical agents.

Brief Description of the Prior Art

In the literature, quaternary 3,4-dihydroisoquinolinium salts have already been described. See, for example, Chim. Ther. 6, 358–366 and 462–468 (1971). J. Chem. Soc. Chem. Commun. 19, 740–741 (1973), Can. J. Chem. 58, 2770–2779 (1980) and J. Org. Chem. 45, 3176–3181 (1980). These compounds are intermediate products, inter alia, for the preparation of 1,2,3,4-tetrahydroisoquinolines having valuable pharmacological properties.

SUMMARY OF THE INVENTION

It has now been found that the 3,4-dihydroisoquinolinium salts of formula (I):

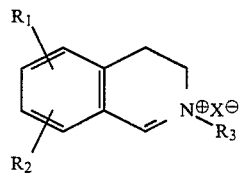

wherein $R_1$ and $R_2$, are each independently hydrogen, $C_1$–$C_3$ alkyl or $C_1$–$C_3$ alkoxy and $R_3$ is a $C_7$–$C_9$ aralkyl, the phenyl nucleus of which can be mono-, di- or trisubstituted by halogen, $C_1$–$C_3$ alkyl or $C_1$–$C_3$ alkoxy and X represents the anion of a physiologically acceptable inorganic or organic acid, have valuable pharmacological properties, particularly an antithrombotic effect.

The present invention thus relates to pharmaceutical compositions with antithrombotic properties containing a compound of formula I and one or more carriers and/or diluents and to the preparation and use thereof.

Examples of $R_1$ to $R_3$ and X include compounds wherein $R_1$ and $R_2$ can each independently be hydrogen, methyl, ethyl, n-propyl, isopropyl, methoxy, ethoxy, n-propoxy or isopropoxy;

$R_3$ can be benzyl, 1-phenylethyl, 2-phenylethyl, 1-phenyl-n-propyl, 2-phenyl-n-propyl, 3-phenyl-n-propyl, 1-methyl-2-phenyl-ethyl, fluorobenzyl, chlorobenzyl, bromobenzyl, difluorobenzyl, dichlorobenzyl, dibromobenzyl, methylbenzyl, ethylbenzyl, isobropylbenzyl, dimethylbenzyl, ethyl-methylbenzyl, trimethylbenzyl, methoxybenzyl, dimethoxybenzyl, trimethoxybenzyl, ethoxybenzyl, diethoxybenzyl, chloro-methyl-benzyl, chloro-methoxy-benzyl, bromo-chlorobenzyl, bromo-methyl-benzyl, bromo-methoxybenzyl, 2-(chlorophenyl)-ethyl, 2-(bromophenyl)-ethyl, 2-(methyl-phenyl)-ethyl, 2-(methoxy-phenyl)-ethyl, 3-(chlorophenyl)-n-propyl, 3-(bromophenyl)-n-propyl, 3-(methylphenyl)-n-propyl or 3-(methoxyphenyl)-n-propyl; and hydrochloric, hydrobromic, sulphuric, phosphoric, acetic or p-toluene-sulphonic acid addition salts thereof.

Preferred compounds of formula I above are those where $R_1$ and $R_2$ are each independently hydrogen, methyl or methoxy and $R_3$ is benzyl, fluorobenzyl, chlorobenzyl, bromobenzyl, methoxybenzyl or trimethoxybenzyl, particularly the compounds wherein $R_1$ and $R_2$ are each methoxy, and $R_3$ is 2-chlorobenzyl, 2-methoxybenzyl or 3,4,5-tri-methoxybenzyl.

DETAILED DESCRIPTION OF THE INVENTION

The compounds of the general formula above can be obtained, for example, by the following processes:

(a) Combining a 3,4-dihydro-isoquinoline of formula (II) wherein $R_1$ and $R_2$ are as defined above with a compound of formula III, wherein $R_3$ is as defined above, in a reaction which is illustrated as follows:

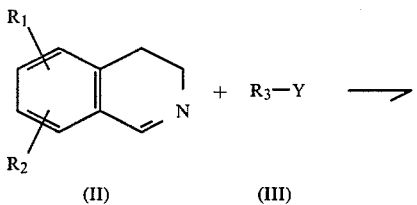

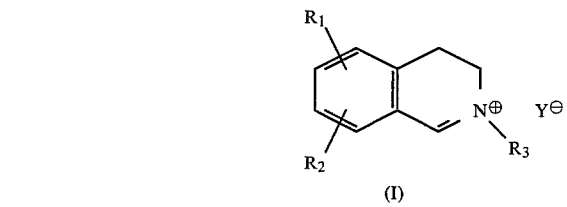

Y is a nucleophilically exchangeable group such as halogen, e.g. a chlorine, bromine or iodine, or a sulphonic acid group or a methanesulphonyloxy or p-toluenesulfonyloxy group.

The reaction is conveniently carried out in a solvent or mixture of solvents such as diethyl ether, tetrahydrofuran, dioxan, toluene, ethyl acetate, methylene chloride, ethylene chloride, chloroform, ethanol, isopropanol, acetonitrile or tetrahydrofuran/toluene at temperatures of between 0° and 150° C., but preferably at temperatures of between 10° and 60° C. However, the reaction may also be carried out without a solvent.

(b) Cyclising an N-formyl compound of formula

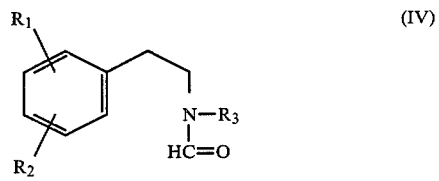

optionally formed in the reaction mixture, wherein $R_1$ to $R_3$ are as defined above, in the presence of an acidic condensing agent.

Suitable acidic condensing agents include polyphosphoric acid, concentrated sulphuric acid or phosphorus oxychloride, optionally in a solvent such as toluene, chlorobenzene, xylene or dichlorobenzene at elevated temperatures, e.g. at temperatures of between 50° C. and the boiling temperature of the reaction mixture. However, the reaction may also be carried out without a solvent.

If a compound of formula I is obtained according to process (a) or (b) with an anion other than the desired anion this compound can be converted into the desired compound by converting it into its base, e.g. using an alkali metal hydroxide such as sodium hydroxide or potassium hydroxide solution, and subsequently treating the base with a corresponding acid.

The compounds of general formulae II to IV used as starting materials are known from the literature or may be obtained by methods known from the literature. Thus, a 3,4-dihydroisoquinoline of general formula II is obtained by cyclising a corresponding N-formyl-2-phenylethylamine and a compound of general formula IV is obtained by formylating a corresponding N-aralkyl-2-phenylethylamine.

As already mentioned hereinbefore, the compounds of general formula I have valuable pharmacological properties, namely an antithrombotic activity, in particular, in addition to an inhibiting effect on the tendency to aggregation of tumor cells.

For example, the following compounds:

A = 2-(2-Chlorobenzyl)-6,7-dimethoxy-3,4-dihydro-isoquinolinium hydrogensulphate,
B = 2-(2-Chlorobenzyl)-3,4-dihydro-isoquinolinium hydrogensulphate and
C = 2-(3,4,5-Trimethoxybenzyl)-6,7-dimethoxy-3,4-dihydro-isoquinolinium chloride were tested for their biological properties as follows:

1. Antithrombotic activity (see BORN and CROSS, J. Physiol. 170, 397 (1964)):

Groups of three male rats weighing about 500 g are given the test substances, suspended in 1% tylose (A and B) or in distilled water (C), in a volume of 0.2 ml per 100 g of the weight of the animal, by esophageal tube. Shortly before the blood samples are taken (1 hour after administration of the substance) the animals are anesthetised with sodium pentobarbital (50 mg/kg i.p.). After the abdomen has been opened up, the required quantity of blood is taken by puncturing the aorta.

The blood is treated with sodium citrate (0.2% final concentration) to prevent it coagulating. Since the aggregation before and after administration of the substance in rats cannot be measured in the same animal, sets of animals from which the plasma has been pooled are compared. In this way, multiple measurements can be made.

Thrombocyte aggregation is measured in platelet-rich plasma (PRP) (quantity of plasma for each test: 1 ml). In order to obtain the PRP, the blood is centrifuged for 10 minutes at 1,000 to 1,200 revolutions per minute (approx. 150 g). The low-platelet plasma for calibrating the aggregometer is obtained by centrifuging (4,000 rpm for 10 minutes).

The pattern of the decrease in optical density of the platelet suspension after the addition of collagen is measured photometrically and recorded. The height of the curve in mm measured at the moment of maximum light transmittance is the measurement of the intensity of aggregation. A 6-channel aggregometer is used for the measurements.

The quantity of collagen (2 to 5 μl/ml of plasma) is such that an irreversible reaction curve is obtained.

The sets of animals treated with the substance are compared with untreated control groups.

| Substance | Dosage mg/kg p.o. | Intensity of Aggregation, mm Height of curve (opt. density) | | Percentage inhibition of aggregation |
|---|---|---|---|---|
| | | Control | Substance | |
| A | 10 | 130 | 69 | 47 |
| B | 5 | 108 | 0 | 100 |
| | 10 | 110 | 0 | 100 |

| Substance | Dosage mg/kg p.o. | Intensity of Aggregation, mm Height of curve (opt. density) | | Percentage inhibition of aggregation |
|---|---|---|---|---|
| | | Control | Substance | |
| C | 5 | 113 | 10 | 89 |

2. Acute toxicity:

Compounds A, B and C are well tolerated, since they do not show any toxic side effects at the maximum dosages administered (10 mg/kg p.o.).

The approximate acute toxicity of substance B is tested on the mouse after oral administration of a dosage of 250 mg/kg to a group of 10 animals. None of the animals died during the observation period of 14 days.

According to the invention, in view of their pharmacological properties, the compounds of general formula I are suitable for the prophylaxis of thromboembolic diseases such as coronary infarct, cerebral infarct, so called transient ischaemic attacks, amaurosis fugax and for the prophylaxis of arteriosclerosis and metastasis formation.

For this purpose, they may be processed together with one or more inert conventional carriers and/or diluents, e.g. corn starch, lactose, glucose, microcrystalline cellulose, magnesium stearate, polyvinyl pyrrolidone, citric acid, tartaric acid, water/ethanol, water/glycerol, water/sorbitol, water/polyethylene glycol, propylene glycol, cetyl stearyl alcohol, carboxymethyl cellulose or fatty substances such as hard fat, paraffin, polyoxyethylene stearate, decyl oleate, spermaceti, sorbitan monostearate or suitable mixtures thereof, optionally in conjunction with other active substances, to form the conventional galenic preparation such as coated tablets, plain tablets, capsules, suppositories, ampoules, drops or suspensions. The daily dosage for adults is appropriately 500 to 1,000 mg, preferably 600 to 900 mg, divided into 2 to 4 individual doses.

The examples which follow illustrate the invention:

EXAMPLE A 6,7-Dimethoxy-3,4-dihydro-isoquinoline (a) N-Formyl-2-(3,4-dimethoxyphenyl)-ethylamine First, 2-(3,4-dimethoxyphenyl)-ethylamine (181.2 g, 1 mol) and chloral hydrate (181 g, 1.1 mol) are mixed together and heated to 120° C., with stirring, for 20 minutes and any volatile components (chloroform and water) are eliminated in a water jet vacuum at an oil bath temperature of 140° C. An oil is left behind which is further processed without any purification.

(b) 6,7-Dimethoxy-3,4-dihydroisoquinoline

The N-formyl-2(3,4-dimethoxy-phenyl)-ethylamine so obtained is stirred with polyphosphoric acid (1 kg) and heated to 140° C. (oil bath temperature). The reaction mixture foams vigorously starting from an internal temperature of 70° C. After 30 minutes, an internal temperature of about 140° C. is attained. The mixture is then poured onto water (1 liter) and made alkaline with concentrated ammonia (1.8 liters) while ice is added. The reaction product is extracted repeatedly with ethyl acetate, the ethyl acetate phase is washed with water, dried, over magnesium sulphate and evaporated giving the title compound (142.5 g) as an oil.

For further purification, the base is dissolved in ethanol (350 ml) and mixed with concentrated sulphuric acid (40 ml). The salt precipitate is cooled, suction filtered, washed with cold ethanol and dried (circulating air dryer, 60° C.) to give 179.5 g of the hydrogensulphate; m.p. 185°–187° C.

The following compounds are obtained analogously:
3,4-Dihydroisoquinoline
Bp$_{208\ Pa}$: 110° C.
6-Methoxy-3,4-dihydroisoquinoline
Melting point of the hydrogensulphate: 166°–168° C. (from ethanol)
5-Methyl-3,4-dihydroisoquinoline
Melting point of the hydrogensulphate: 188°–190° C. (from ethanol)
6,7-Dimethyl-3,4-dihydroisoquinoline
Melting point of the hydrogensulphate: 183°–185° C. (from ethanol)

EXAMPLE B 2-(2-Chlorobenzyl)-6,7-dimethoxy-3,4-dihydroisoquinolinium hydrogensulphate First, 6,7-dimethoxy-3,4-dihydro-isoquinoline hydrogensulphate (173.7, 0.6 mol) is dissolved in water (300 ml) and converted into the free base by means of concentrated ammonia. The free base is then extracted 4 times with ethyl acetate. The ethyl acetate phase is washed with water and dried and concentrated by evaporation in vacuo. The base so obtained (108.3 g=0.57 mol) is dissolved in dry dioxan (300 ml) and 2-chlorobenzyl chloride (100 g, 0.62 mol) is added. After about 10 minutes, the 6,7-dimethoxy-3,4-dihydroisoquinolinium chloride begins to precipitate. It is stirred for 4 days at ambient temperature and on the third day a further 10 ml (12.7g) of 2-chlorobenzyl chloride is added.

After 4 days, the salt is suction filtered, washed with dioxan and ether and dried to give 177.1 g of dry salt, m.p. 196° C. (from ethanol/ethyl acetate).

Elemental Analysis $C_{18}H_{19}Cl_2NO_2$: Calculated: C, 61.37; H, 5.44; N, 3.98; Cl, 20.13. Found: C, 61.24; H, 5.63; N, 3.88; Cl, 19.98.

In order to convert it into the hydrogensulphate, the chloride is dissolved in water and made alkaline with 15N sodium hydroxide solution, whereupon a thick precipitate is formed. This is extracted with chloroform, washed, dried and evaporated. The residue obtained is dissolved in isopropanol (450 ml) and mixed with conc. sulphuric acid (27.5 ml). The salt is precipitated in crystalline form, cooled, suction filtered, washed with cold isopropanol and ether and dried to give 138.4 g, m.p. 227°–229° C. (from methanol)

Elemental Analysis $C_{18}H_{20}ClNO_6S$: Calculated: C, 52.24; H, 4.87; N, 3.38; Cl, 8.57; S, 7.75. Found: C, 52.51; H, 4.85; N, 3.41; Cl, 8.62; S, 7.93.

EXAMPLE C 2-(2-Chlorobenzyl)-3,4-dihydroisoquinolinium hydrogen-sulphate

The title compound is prepared analogously to Example A from 3,4-dihydroisoquinoline and 2-chlorobenzyl chloride in acetonitrile. The melting point of the hydrogensulphate is 190°–192° C. (from isopropanol).

Elemental Analysis $C_{16}H_{16}ClNO_4S$: Calculated: C, 54.31; H, 4.56; N, 3.96; Cl, 10.02; S, 9.06. Found: C, 54.00; H, 4.72; N, 3.96; Cl, 10.05; S, 9.01.

EXAMPLE D 2-(2-Chlorobenzyl)-5-methyl-3,4-dihydroisoquinolinium chloride

The title compound is prepared analogously to Example A from 5-methyl-3,4-dihydro-isoquinoline and 2-chlorobenzyl chloride in dioxan. Melting point: 166°–168° C.

EXAMPLE E 2-(2-Chlorobenzyl)-6,7-dimethyl-3,4-dihydroisoquinolinium chloride The title compound is prepared analogously to Example A from 6,7-dimethyl-3,4-dihydroisoquinoline and 2-chlorobenzyl chloride in dioxan. Melting point: 127°–129° C.

EXAMPLE F ps 2-(2-Chlorobenzyl)-6-methoxy-3,4-dihydroisoquinolinium chloride The title compound is prepared analogously to Example A from 6-methoxy-3,4-dihydro-isoquinoline and 2-chlorobenzyl chloride in ethylene chloride. Melting point: 156°–158° C. (Decomp., from dioxan).

EXAMPLE G

2-Benzyl-6,7-dimethoxy-3,4-dihydroisoquinolinium chloride

The title compound is prepared analogously to Example A from 6,7-dimethoxy-3,4-dihydroisoquinoline and benzyl chloride in dioxan. The melting point: 181°–183° C. (Decomp.)

Elemental Analysis $C_{18}H_{20}ClNO_2$: Calculated: C, 68.02; H, 6.34; N, 4.41; Cl, 11.16. Found: C, 67.81; H, 6.16; N, 4.35; Cl, 11.05.

EXAMPLE H 2-(2-Fluorobenzyl)-6,7-dimethoxy-3,4-dihydroisoquinolinium chloride The title compound is prepared analogously to Example A from 6,7-dimethoxy-3,4-dihydroisoquinoline and 2-fluorobenzyl chloride in ethylene chloride. Melting point: 196°–198° C. (Decomp.)

Elemental Analysis $C_{18}H_{19}ClFNO_2$: Calculated: N, 4.17; Cl, 10.56. Found: N, 4.05; Cl, 10.60.

EXAMPLE I 2-(2-Methylbenzyl)-6,7-dimethoxy-3,4-dihydroisoquinolinium chloride The title compound is prepared analogously to Example A from 6,7-dimethoxy-3,4-dihydroisoquinoline and 2-methyl-benzyl chloride in dioxan. Melting point: 193°–195° C. (Decomp., from ethanol-ether).

Elemental Analysis $C_{19}H_{22}ClNO_2$: Calculated: N, 4.22; Cl, 10.67. Found: N, 3.96; Cl, 10.47.

EXAMPLE J 2-(4-Methylbenzyl)-6,7-dimethoxy-3,4-dihydroisoquinolinium chloride The title compound is prepared analogously to Example A from 6,7-dimethoxy-3,4-dihydro-isoquinoline and 4-methylbenzyl chloride in ethylene chloride. Melting point: 181°–183° C. (Decomp.)

EXAMPLE K 2-(4-Chlorobenzyl)-6,7-dimethoxy-3,4-dihydroisoquinolinium chloride The title compound is prepared analogously to Example A from 6,7-dimethoxy-3,4-dihydroisoquinoline and 4-chlorobenzyl chloride in ethylene chloride. Melting point: 182°–184° C. (Decomp.)

Elemental Analysis $C_{18}H_{19}Cl_2NO_2$: Calculated: C, 61.37; H, 5.44; N, 3.98; Cl, 20.13. Found: C, 61.76; H, 5.46; N, 3.93; Cl, 20.50.

EXAMPLE L 2-(3,4,5-Trimethoxybenzyl)-6,7-dimethoxy-3,4-dihydroisoquinolinium chloride The title compound is prepared analogously to Example A from 6,7-dimethoxy-3,4-dihydroisoquinoline and 3,4,5-trimethoxybenzyl chloride in dioxan. Melting point: 187°–189° C. (Decomp.)

Elemental Analysis $C_{21}H_{26}ClNO_5$: Calculated: N 3.43; Cl, 8.69. Found: N 3.44; Cl, 8.66.

EXAMPLE M 2-(2-Chlorobenzyl)-6,7-dimethoxy-3,4-dihydroisoquinolinium hydrogensulphate (a) N-(2-Chlorobenzyl)-2-(3,4-dimethoxyphenyl)-ethylamine 2-(3,4-Dimethoxyphenyl)-ethylamine (80.3 g, 0.443 mol) and o-chlorobenzaldehyde (62 g, 0.443 mol) are boiled (1 hour) in toluene (500 ml) using a water separator. The reaction mixture is evaporated, the oily residue is taken up in methanol (500 ml) and combined, under vigorous stirring and intensive cooling, with a solution of sodium borohydride (16.9 g, 0.443 mol) in water (50 ml). After it has all been added, the resulting mixture is stirred (1 hour) at ambient temperature, concentrated in vacuo and the residue is distilled in vacuo. Yield: 108.8 g. $Bp_{16.9\ Pa}$: 188°–190° C.

(b) N-Formyl-N(2-chlorobenzyl)-2(3,4-dimethoxyphenyl)-ethylamine

N-(2-chlorobenzyl)-2-(3,4-dimethoxy-phenyl)-ethylamine (88.4 g, 0.29 mol) is mixed with chloral hydrate (52.5 g, 0.34 mol) and heated (120° C.) for 30 minutes. After cooling, ethyl acetate is added and the mixture is washed with water, dried and evaporated. Yield: 103 g.

(c) 2-(2-Chlorobenzyl)-6,7-dimethoxy-3,4-dihydroisoquinolinium hydrogensulphate

N-Formyl-N(2-chlorobenzyl)-2(3,4-dimethoxyphenyl)-ethylamine (12.1 g) are dissolved in toluene (50 ml), combined with phosphorus oxychloride (15.2 g = 9 ml) and heated under reflux for 1.5 hours. The mixture is concentrated, the residue is mixed with ice, made alkaline with potassium carbonate and extracted with ethyl acetate. The ethyl acetate extract is concentrated by evaporation. The residue obtained is dissolved in isopropanol and mixed with conc. sulphuric acid (2 ml). After cooling, the mixture is suction filtered, washed with isopropanol and ether and dried. Yield: 8.6 g. Melting point: 226°–228° C.

Elemental Analysis $C_{18}H_{20}ClNO_6S$: Calculated: C, 52.24; H, 4.87; N, 3.38; Cl, 8.57; S, 7.75. Found: C, 52.44; H, 4.92; N, 3.35; Cl, 8.43; S, 7.98.

EXAMPLE 1

Tablets containing 300 mg of 2-(2-chlorobenzyl)-6,7-dimethoxy-3,4-dihydro-isoquinolinium hydrogensulphate

| Composition: 1 tablet contains: | |
|---|---|
| Active substance | 300.0 mg |
| Lactose | 120.0 mg |
| Microcrystalline cellulose | 100.0 mg |
| Corn starch | 72.0 mg |
| Polyvinyl pyrrolidone | 6.0 mg |
| Magnesium stearate | 2.0 mg |
| | 600.0 mg |

Preparation

The active substance is mixed with lactose, cellulose and corn starch and granulated with a 15% solution of polyvinyl pyrrolidone in water. The moist mass is passed through a screen, spread out on drying racks and dried at 45° C. After it has been screened again, magnesium stearate is added and the mixture is compressed to form tablets.

Weight of tablet: 600 mg

Punch: 13 mm in diameter, biplanar, faceted on both sides and notched on one side.

EXAMPLE 2

Coated tablets containing 250 mg of 2-(2-chlorobenzyl)-6,7-dimethoxy-3,4-dihydro-isoquinolinium hydrogensulphate

| 1 tablet core contains: | |
|---|---|
| Active substance | 250.0 mg |
| Lactose | 100.0 mg |
| Microcrystalline cellulose | 40.0 mg |
| Corn starch | 84.0 mg |
| Polyvinyl pyrrolidone | 5.0 mg |
| Magnesium stearate | 1.0 mg |
| | 480.0 mg |

Preparation

The mixture for compression is prepared as in Example 1.

Weight of core: 480 mg

Punch: 11 mm, convex, with a radius of curvature of 10 mm.

The tablet cores are coated with a layer of sugar in known manner in a coating pan.

Weight of coated tablet: 560 mg

EXAMPLE 3

Suppositories containing 400 mg of 2-(2-chlorobenzyl)-6,7-dimethoxy-3,4-dihydro-isoquinolinium hydrogensulphate

| 1 suppository contains: | |
|---|---|
| Active substance | 0.40 g |
| Suppository mass (e.g. Witepsol H 19 and Witepsol W 45) | 1.30 g |
| | 1.70 g |

Preparation

The hard fat is melted. At 38° C. the ground active substance is homogeneously dispersed in the melt. It is cooled to 35° C. and poured into slightly chilled suppository moulds.

Weight of suppository: 1.7 g

What is claimed is:

1. A pharmaceutical composition containing an amount effective to prevent or treat a thromboembolic disease of a 3,4-dihydroisoquinolinium salt of formula I

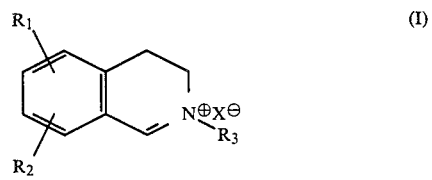

wherein
- R₁ and R₂ are each independently hydrogen, $C_1$–$C_3$ alkyl or $C_1$–$C_3$ alkoxy;
- R₃ is a $C_7$–$C_9$ aralkyl, the phenyl nucleus of which can be mono-, di- or trisubstituted by halogen, $C_1$–$C_3$ alkyl or $C_1$–$C_3$ alkoxy; and
- X represents the anion of a pharamaceutically acceptable inorganic or organic acid, together with one or more pharmaceutically acceptable carriers or diluents.

2. A pharmaceutical composition as claimed in claim I, containing a 3,4-dihydro-isoquinolinium salt of general formula I as claimed in claim 1, wherein
- R₁ and R₂, are each independently hydrogen methyl or methoxy,
- R₃ is a benzyl, fluorobenzyl, chlorobenzyl, bromobenzyl, methoxybenzyl or trimethoxybenzyl group and
- X represents the anion of a physiologically acceptable inorganic or organic acid, together with one or more inert carriers and/or diluents.

3. A pharmaceutical composition as claimed in claim 1, containing a 3,4-dihydro-isoquinolinium salt of general formula I as claimed in claim 1, wherein
- R₁ and R₂ each is a methoxy group,
- R₃ is a 2-chlorobenzyl, 2-methoxybenzyl or 3,4,5-trimethoxybenzyl group and
- X represents the anion of a physiologically acceptable acid, in addition to one or more inert carriers and/or diluents.

4. A pharmaceutical composition as claimed in claim 1, containing 2-(2-chlorobenzyl)-6,7-dimethoxy-3,4-dihydro-isoquinolinium hydrogensulphate in addition to one or more inert carriers and/or diluents.

5. A pharmaceutical composition as claimed in claim 1, containing 2-(2-chlorobenzyl)-3,4-dihydro-isoquinolinium hydrogensulphate in addition to one or more inert carriers and/or diluents.

6. A pharmaceutical composition as claimed in claim 1, containing 2-(3,4,5-trimethoxybenzyl)-6,7-dimethoxy-3,4-dihydroisoquinolinium hydrochloride in addition to one or more inert carriers and/or diluents.

7. A method of treating a thromboembolic disease in a mammal in need thereof which comprises administrering a therapeutically effective amount of a composition of any of claims 1–6 to said mammal.

8. The method of claim 7 which comprises treating a thromboembolic disease selected from coronary infarct, cerebral infarct, transient ischemic attacks, amaurosis fugax, arteriosclerosis and metastasis formation.

9. A pharmaceutical composition comprising from about 125 mg to about 500 mg of a 3,4-dihydroisoquinolinium salt of formula I:

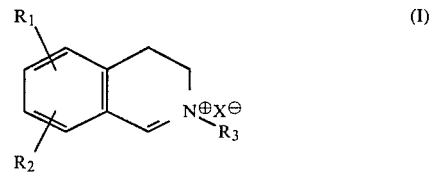

wherein
- R₁ and R₂ are each independently hydrogen, $C_1$–$C_3$ alkyl or $C_1$–$C_3$ alkoxy;
- R₃ is a $C_7$–$C_9$ aralkyl, the phenyl nucleus of which can be mono-, di- or trisubstituted by halogen, $C_1$–$C_3$ alkyl or $C_1$–$C_3$ alkoxy, and X represents the anion of a pharmaceutically acceptable inorganic or organic acid, together with one or more carriers or diluents.

10. A pharmaceutical composition of claim 9, wherein the 3,4-dihydroisoquinolinium salt is selected from:
- 2-(2-chlorobenzyl)-6,7-dimethoxy-3,4-dihydroisoquinolinium hydrogensulphate;
- 2-(2-chlorobenzyl)-3,4-dihydroisoquinolium hydrogensulphate; and
- 2-(3,4,5-trimethoxybenzyl)-6,7-dimethoxy-3,4-dihydroisoquinolinium hydrochloride.

11. A method of treating a thromboembolic disease in an individual in need thereof which method comprises administering to said individual a therapeutically effective amount of a pharmaceutical composition of any of claims 9 or 10.

12. A method of preventing thromboembolic disease in an individual in need thereof, which method comprises administering to said individual a prophylactically effective amount of a pharmaceutical composition of claim 1.

13. A method of preventing thromboembolic disease in an individual in need thereof, which method comprises administering to said individual a prophylactically effective amount of a pharmaceutical composition of claim 9.

14. A method of preventing thromboembolic disease in an individual in need thereof, which method comprises administering daily to said individual a prophylactically effective amount of a pharmaceutical composition of claim 1.

15. A method of preventing thromboembolic disease in an individual in need thereof, which method comprises administering daily to said individual a prophylactically effective amount of a pharmaceutical composition of claim 9.

* * * * *